(12) United States Patent
Bonyak et al.

(10) Patent No.: US 8,333,103 B2
(45) Date of Patent: Dec. 18, 2012

(54) CALIBRATION OF A FORCE MEASURING SYSTEM FOR LARGE BEND ANGLES OF A CATHETER

(75) Inventors: Yevgeny Bonyak, Haifa (IL); Doron Ludwin, Haifa (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 86 days.

(21) Appl. No.: 13/075,655

(22) Filed: Mar. 30, 2011

(65) Prior Publication Data

US 2012/0253167 A1    Oct. 4, 2012

(51) Int. Cl.
*G12B 13/00* (2006.01)
*A61M 25/16* (2006.01)

(52) U.S. Cl. .................. 73/1.79; 73/1.01; 73/1.75

(58) Field of Classification Search .............. 73/1.01, 73/1.75, 1.79, 1.81; 600/101, 117
See application file for complete search history.

(56) References Cited

U.S. PATENT DOCUMENTS

| | | | |
|---|---|---|---|
| 5,391,199 A | 2/1995 | Ben-Haim | |
| 5,558,091 A * | 9/1996 | Acker et al. | 600/424 |
| 5,833,608 A * | 11/1998 | Acker | 600/409 |
| 6,177,792 B1 * | 1/2001 | Govari et al. | 324/207.12 |
| 6,201,387 B1 * | 3/2001 | Govari | 324/207.17 |
| 6,203,493 B1 * | 3/2001 | Ben-Haim | 600/117 |
| 6,239,724 B1 | 5/2001 | Doron et al. | |
| 6,272,371 B1 | 8/2001 | Shlomo | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,711,429 B1 * | 3/2004 | Gilboa et al. | 600/407 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2004/0244464 A1 * | 12/2004 | Hajdukiewicz et al. | 73/1.79 |

(Continued)

FOREIGN PATENT DOCUMENTS

EP    2196143 A1    6/2010

(Continued)

OTHER PUBLICATIONS

EP Search Report Appln No. 12 16 1784 dated Jul. 11, 2012.

*Primary Examiner* — David Rogers
(74) *Attorney, Agent, or Firm* — William A. Schoneman

(57) ABSTRACT

A method for calibrating a force measuring probe comprises providing a probe having an insertion tube with a distal tip, a joint comprising a resilient member, a joint sensor in conjunction with a processor coupled to the probe wherein the processor has a memory of an axial displacement threshold for the joint stored therein; applying force to the distal tip; measuring the displacement and deflection of the distal tip; correlating the measured displacement and deflection of the distal tip to the applied force and storing the correlation in the memory until reaching the axial displacement threshold; applying force greater than the axial displacement threshold to the distal tip to define a new force value; measuring the position of the distal tip in a plane transverse to the direction of force exerted on the distal tip; correlating the measured position of the distal tip in the plane transverse to the direction of force to the new force value and storing the correlation in the memory until reaching a pre-established upper limit for the new force value.

7 Claims, 5 Drawing Sheets

U.S. PATENT DOCUMENTS

| | | | |
|---|---|---|---|
| 2004/0254458 A1* | 12/2004 | Govari | 600/437 |
| 2007/0100332 A1 | 5/2007 | Paul et al. | |
| 2007/0185397 A1* | 8/2007 | Govari et al. | 600/424 |
| 2009/0093806 A1 | 4/2009 | Govari et al. | |
| 2009/0138007 A1 | 5/2009 | Govari et al. | |

FOREIGN PATENT DOCUMENTS

| | | |
|---|---|---|
| EP | 2338411 A1 | 6/2011 |
| EP | 2338412 A1 | 6/2011 |
| WO | WO 96/05768 | 2/1996 |

* cited by examiner

US 8,333,103 B2

CALIBRATION OF A FORCE MEASURING SYSTEM FOR LARGE BEND ANGLES OF A CATHETER

FIELD OF THE INVENTION

The present invention relates generally to invasive medical devices, and specifically to methods and devices for sensing displacement of a joint in a probe, such as a catheter, that is applied to the body of a patient, and for measuring force exerted on the distal end or tip of the catheter, particularly force resulting in extreme or large bend angles at the catheter distal end.

BACKGROUND OF THE INVENTION

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue.

A number of patent publications describe catheters with integrated pressure sensors for sensing tissue contact. As one example, U.S. Patent Application Publication 2007/0100332, whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

To date, there have been no known devices or methods for accurately sensing displacement of a joint in a device, such as a catheter, and for measuring force exerted on the distal end or tip of the device, particularly force resulting in extreme or large bend angles at the distal end of the device.

SUMMARY OF THE INVENTION

The present invention is directed to a method for calibrating a force measuring probe used in a medical procedure performed on a body of a patient. The method comprises the steps of providing a probe, comprising an insertion tube, having a longitudinal axis and a distal end, a distal tip disposed at the distal end of the insertion tube and is configured to be brought into contact with tissue of the body, a joint comprising a resilient member, which is configured to deform in response to force exerted on the distal tip when the distal tip engages tissue, the joint coupling the distal tip to the distal end of the insertion tube, and a joint sensor, contained within the probe, for sensing a position of the distal tip relative to the distal end of the insertion tube, the joint sensor comprising a first subassembly and a second subassembly, which are disposed within the probe on opposite, respective sides of the joint, wherein the first subassembly and the second subassembly comprise one or more magnetic transducers.

A processor is coupled to the probe for applying a current to one of the first subassembly and the second subassembly, thereby causing one of the first subassembly and the second subassembly to generate at least one magnetic field, and which is coupled to receive and process one or more signals output by the other of the first subassembly and the second subassembly responsively to the at least one magnetic field so as to detect changes in a position of the distal tip relative to the distal end of the insertion tube, wherein the changes in the position of the distal tip detected by the processor comprise an axial displacement of the distal tip and an angular deflection of the distal tip relative to the distal end of the insertion tube, and wherein the processor is configured to generate, responsively to the detected changes in the position, an output that is indicative of the force exerted on the distal tip, and a memory having an axial displacement threshold for the joint stored therein.

Force is applied to the distal tip and axial displacement and the angular deflection of the distal tip are measured. The next step is correlating the measured axial displacement and the angular deflection of the distal tip to the applied force at the distal tip and storing the correlation in the memory until reaching the axial displacement threshold.

Once this is achieved, force greater than the axial displacement threshold is applied to the distal tip to define a new force value and the position of the distal tip in a plane transverse to the direction of force exerted on the distal tip is measured.

The measured position of the distal tip in the plane transverse to the direction of force is then correlated to the new force value and the correlation is stored in the memory until reaching a pre-established upper limit for the new force value.

The present invention will be more fully understood from the following detailed description of the embodiments thereof, taken together with the drawings in which:

DETAILED DESCRIPTION OF THE INVENTION

Figure 1:
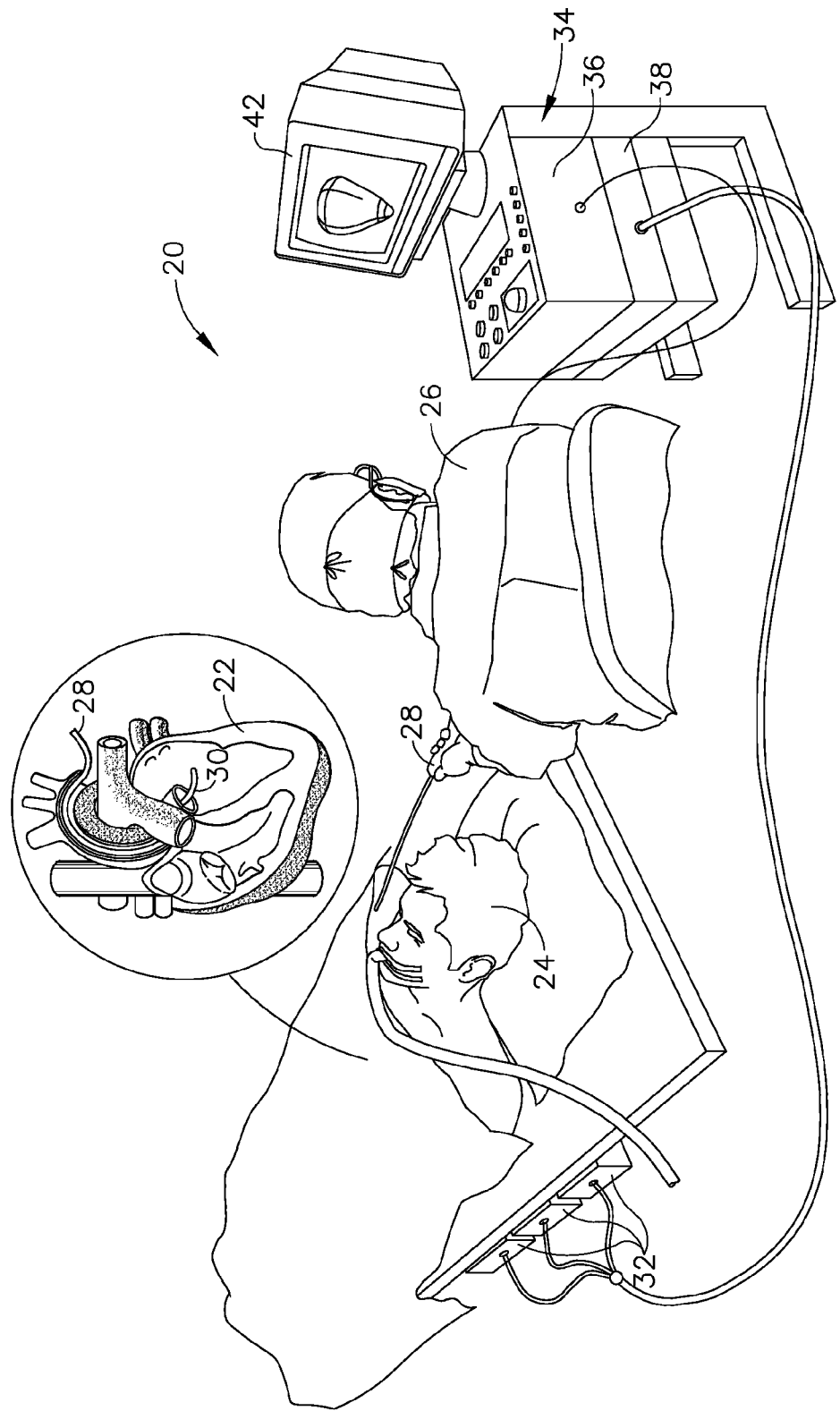
FIG. 1 is a schematic, pictorial illustration of a catheter-based medical system, in accordance with an embodiment of the present invention.

This application uses the technical disclosure of commonly owned pending U.S. patent application Ser. No. 11/868,733, filed Oct. 8, 2007, and U.S. patent application Ser. No. 12/327,226, filed Dec. 3, 2008 which are assigned to the assignee of the present patent application and whose disclosure of both references is incorporated herein by reference. Accordingly, like or similar features are identified using the same reference numerals from U.S. patent application Ser. No. 12/327,226.

The above-mentioned U.S. patent application Ser. No. 11/868,733 describes a catheter whose distal tip is coupled to the distal end of the catheter insertion tube by a spring-loaded joint, which deforms in response to pressure exerted on the distal tip when it engages tissue. A magnetic position sensing assembly within the probe, comprising coils on opposite sides of the joint, senses the position of the distal tip relative to the distal end of the insertion tube. Changes in this relative position are indicative of deformation of the spring and thus give an indication of the pressure.

Embodiments of the present invention that are described hereinbelow provide a design for the sensing assembly and method of calibrating and method of operation, which facilitates precise measurement of tip movement as well as more precise measurement of force. The configuration of the coils in the design in conjunction with the method of calibration and method of operation permit precise sensing as well as precise force measurement at very large deflections and maximum compression of the joint connecting the catheter tip to the insertion tube. Therefore, the pressure on the tip can be accurately measured with enhanced accuracy even at large bend angles for the catheter, thereby allowing the catheter and its method of use to be more accurate and predictive of actual force exerted on the catheter tip even at large or extreme bend angles, i.e. those bend angles resulting in complete or maximum compression of the joint, which will be addressed in greater detail below.

FIG. 1 is a schematic, pictorial illustration of a system 20 for cardiac catheterization, in accordance with an embodiment of the present invention. System 20 may be based, for example, on the CARTO™ system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used, mutatis mutandis, for other therapeutic and/or diagnostic purposes in the heart or in other body organs.

An operator 26, such as a cardiologist, inserts catheter 28 through the vascular system of a patient 24 so that a distal end 30 of the catheter enters a chamber of the patient's heart 22. The operator advances the catheter so that the distal tip of the catheter engages endocardial tissue at a desired location or locations. Catheter 28 is typically connected by a suitable connector at its proximal end to console 34. The console may comprise a radio frequency (RF) generator, which supplies high-frequency electrical energy via the catheter for ablating tissue in the heart at the locations engaged by the distal tip. Alternatively or additionally, the catheter and system may be configured to perform other therapeutic and diagnostic procedures that are known in the art.

Console 34 uses magnetic position sensing to determine position coordinates of distal end 30 of catheter 28 inside heart 22. For this purpose, a driver circuit 38 in console 34 drives field generators 32 to generate magnetic fields in the vicinity of the body of patient 24. Typically, the field generators comprise coils, which are placed below the patient's torso at known positions external to the patient. These coils generate magnetic fields within the body in a predefined working volume that contains heart 22. A magnetic field sensor within distal end 30 of catheter 28 (shown in FIG. 3) generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor may be carried out by dedicated or programmable digital hardware components. Based on the signals received from the catheter and other components of system 20, processor 36 drives a display 42 to give operator 26 visual feedback regarding the position of distal end 30 in the patient's body, as well as regarding displacement of the distal tip of the catheter, and status information and guidance regarding the procedure that is in progress.

Alternatively or additionally, system 20 may comprise an automated mechanism for maneuvering and operating catheter 28 within the body of patient 24. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. These signals are indicative of both the position of the distal end of the catheter and of force exerted on the distal end, as explained further hereinbelow.

Figure 2:
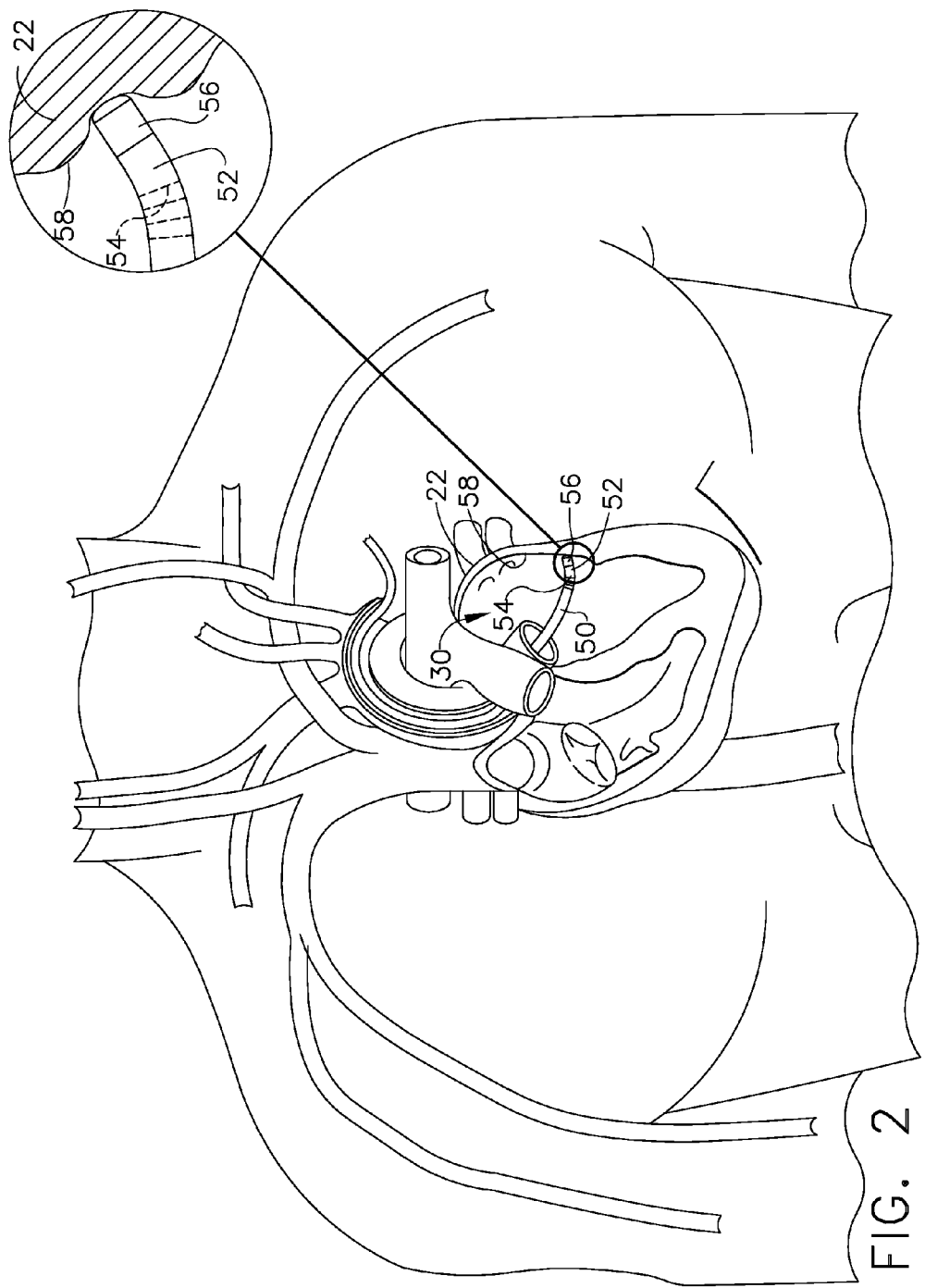
FIG. 2 is a schematic detail view showing the distal tip of a catheter in contact with endocardial tissue, in accordance with an embodiment of the present invention.

FIG. 2 is a schematic sectional view of a chamber of a heart 22, showing distal end 30 of catheter 28 inside the heart, in accordance with an embodiment of the present invention. The catheter comprises an insertion tube 50, which is typically inserted into the heart percutaneously through a blood vessel, such as the vena cava or the aorta. An electrode 56 on a distal tip 52 of the catheter engages endocardial tissue 58. Pressure exerted by the distal tip against the endocardium deforms the endocardial tissue locally, so that electrode 56 contacts the tissue over a relatively large area. In the pictured example, the electrode engages the endocardium at an angle, rather than head-on. Distal tip 52 therefore bends at an elastic joint 54 relative to the distal end of insertion tube 50 of the catheter. The bend facilitates optimal contact between the electrode and the endocardial tissue.

Because of the elastic quality of joint 54, the angle of bending and the axial displacement of the joint are proportional to the pressure exerted by tissue 58 on distal tip 52 (or equivalently, the pressure exerted by the distal tip on the tissue). Measurement of the bend angle and axial displacement thus gives an indication of this pressure. The pressure indication may be used by the operator of catheter 20 is ensuring that the distal tip is pressing against the endocardium firmly enough to give the desired therapeutic or diagnostic result, but not so hard as to cause undesired tissue damage.

Figure 3:
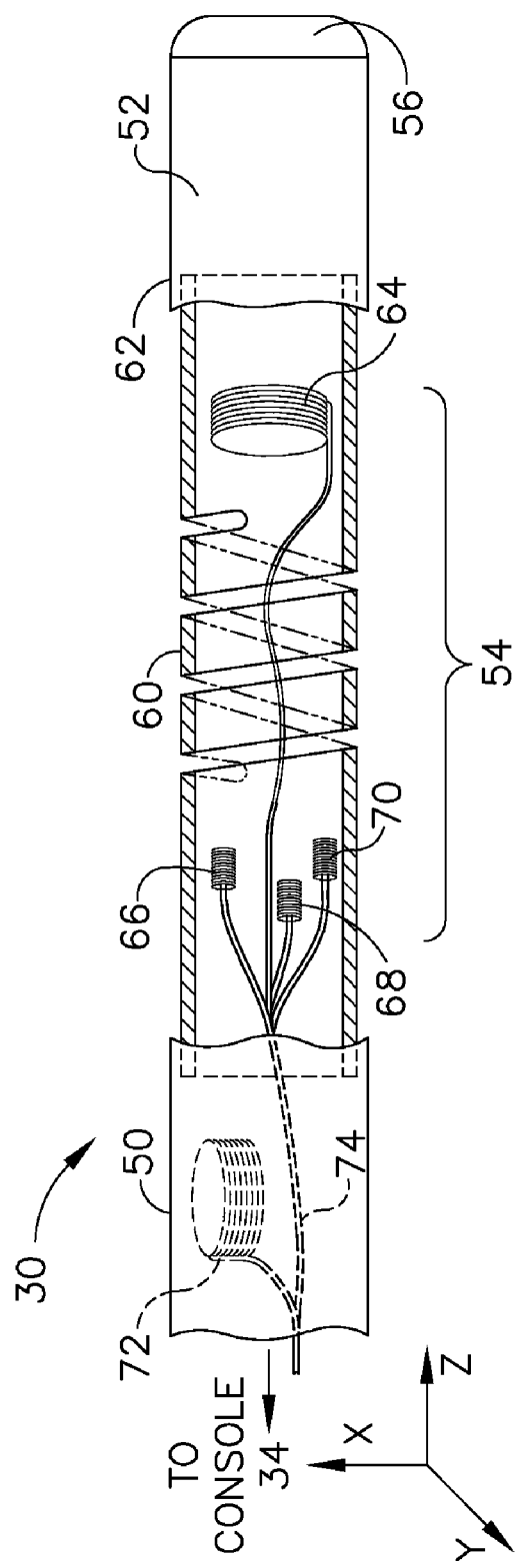
FIG. 3 is a schematic, sectional view showing details of the distal end of a catheter, in accordance with an embodiment of the present invention.

FIG. 3 is a schematic, sectional view of distal end 30 of catheter 28, showing details of the structure of the catheter in accordance with an embodiment of the present invention. Insertion tube 50 is connected to distal tip 52 by joint 54, as noted above. The insertion tube is covered by a flexible, insulating material 62, such as Celcon®, Teflon®, or heat-resistant polyurethane, for example. The area of joint 54 is covered, as well, by a flexible, insulating material, which may be the same as material 62 or may be specially adapted to permit unimpeded bending and compression of the joint. (This material is cut away in FIG. 3 in order to expose the internal structure of the catheter.) Distal tip 52 may be covered, at least in part, by electrode 56, which is typically made of a conductive material, such as a platinum/iridium alloy. Alternatively, other suitable materials may be used, as will be apparent to those skilled in the art. Further alternatively, for some applications, the distal tip may be made without a covering electrode. The distal tip is typically relatively rigid, by comparison with the flexible insertion tube.

Joint 54 comprises a resilient coupling member 60. In this embodiment, the coupling member has the form of a tubular piece of an elastic material, with a helical cut along a portion of its length. For example, the coupling member may comprise a superelastic alloy, such as nickel titanium (Nitinol). The helical cut causes the tubular piece to behave like a spring in response to forces exerted on distal tip 52. Further details regarding the fabrication and characteristics of this sort of coupling member are presented in U.S. patent application Ser. No. 12/134,592, filed Jun. 6, 2008, which is assigned to the assignee of the present patent application and whose disclosure is incorporated herein by reference. Alternatively, the coupling member may comprise a coil spring or any other suitable sort of resilient component with the desired flexibility and strength characteristics.

The stiffness of coupling member 60 determines the range of relative movement between tip 52 and insertion tube 50 in response to forces exerted on the distal tip. Such forces are encountered when the distal tip is pressed against the endocardium during an ablation procedure. The desired pressure for good electrical contact between the distal tip and the endocardium during ablation is on the order of 20-30 grams. The coupling member is configured to permit axial displacement (i.e., lateral movement along the axis of catheter 28) and angular deflection of the distal tip in proportion to the pressure on the tip. Measurement of the displacement and deflection by processor 36 gives an indication of the pressure and thus helps to ensure that the correct pressure is applied during ablation.

A joint sensing assembly, comprising coils 64, 66, 68 and 70 within catheter 28, provides accurate reading of the position of distal tip 52 relative to the distal end of insertion tube 50, including axial displacement and angular deflection. These coils are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The coils in catheter 28 are divided between two subassemblies on opposite sides of joint 54: One subassembly comprises coil 64, which is driven by a current via a cable 74 from console 34 to generate a magnetic field. This field is received by a second subassembly, comprising coils 66, 68 and 70, which are located in a section of the catheter that is spaced axially apart from coil 64. (The term "axial," as used in the context of the present patent application and in the claims, refers to the direction of the longitudinal axis of distal end 30 of catheter 28, which is identified as the Z-direction in FIG. 3. An axial plane is a plane perpendicular to this longitudinal axis, and an axial section is a portion of the catheter contained between two axial planes.) Coils 66, 68 and 70 emit electrical signals in response to the magnetic field generated by coil 64. These signals are conveyed by cable 74 to processor 36, which processes the signals in order to measure the axial displacement and angular deflection of joint 54.

Coils 66, 68 and 70 are fixed in catheter 28 at different radial or angular deflection locations. (The term "radial" or "angular" refers to coordinates relative to the catheter axis, i.e., coordinates in an X-Y plane in FIG. 3.) Specifically, in this embodiment, coils 66, and 70 are all located in the same axial plane at different azimuthal angles about the catheter axis. For example, the three coils may be spaced azimuthally 120° apart at the same radial distance from the axis.

The axes of coils 64, 66, 68 and 70 are parallel to the catheter axis (and thus to one another, as long as joint 54 is undeflected). Consequently, coils 66, 68 and 70 will output strong signals in response to the field generated by coil 64, and the signals will vary strongly with the distances of coils 66, 68 and 70 from coil 64. (Alternatively, the axis of coil 64 and/or coils 66, 68 and 70 may be angled relative to the catheter axis, as long as the coil axes have a sufficient parallel component in order to give substantial signals.) Angular deflection of tip 52 will give rise to a differential change in the signals output by coils 66, 68 and 70, depending on the direction and magnitude of deflection, since one or two of these coils will move relatively closer to coil 64. Compressive displacement of the tip will give rise to an increase in the signals from all of coils 66, 68 and 70.

Processor 36 analyzes the signals output by coils 66, 68 and 70 in order to measure the deflection and displacement of joint 54. The sum of the changes in the signals gives a measure of the compression, while the difference of the changes gives the deflection. The vector direction of the difference gives an indication of the bend direction. A suitable calibration procedure may be used to measure the precise dependence of the signals on deflection and displacement of the joint.

Various other configurations of the coils in the sensing subassemblies may also be used, in addition to the configuration shown and described above. For example, the positions of the subassemblies may be reversed, so that that field generator coil is on the proximal side of joint 54, and the sensor coils are in the distal tip. As another alternative, coils 66, 68 and 70 may be driven as field generators (using time- and/or frequency-multiplexing to distinguish the fields), while coil 64 serves as the sensor. The sizes and numbers of the coils in FIG. 3 are shown only by way of example, and larger or smaller numbers of coils may similarly be used, in various different positions, so long as one of the subassemblies comprises at least two coils, in different radial positions, to allow differential measurement of joint deflection.

Prior calibration of the relation between pressure on tip 52 and movement of joint 54 may be used by processor 36 in translating the coil signals into terms of pressure. By virtue of the combined sensing of displacement and deflection, this pressure sensing system reads the pressure correctly regardless of whether the electrode engages the endocardium head-on or at an angle. The pressure reading is insensitive to temperature variations and free of drift, unlike piezoelectric sensors, for example. Because of the high sensitivity to joint motion that is afforded by the arrangement of coils 64, 66, 68 and 70 that is shown in FIG. 3, processor 36 can measure small displacements and deflections with high precision. Therefore, coupling member 60 can be made relatively stiff, and processor 36 will still be able to sense and measure accurately the pressure on tip 52. The stiffness of the coupling member makes it easier for the operator to maneuver and control the catheter.

One or more of coils 64, 66, 68 and 70 may also be used to output signals in response to the magnetic fields generated by field generators 32, and thus serve as position sensing coils. Processor 36 processes these signals in order to determine the coordinates (position and orientation) of distal end 30 in the external frame of reference that is defined by the field generators. Additionally or alternatively, one or more further coils (or other magnetic sensors) may be deployed in the distal end of the catheter for this purpose. The position sensing coils in distal end 30 of catheter 28 enable console 34 to output both the location and orientation of the catheter in the body and the displacement and deflection of tip 52, as well as the pressure on the tip.

Although the operation of a magnetic position sensing assembly and its use in sensing pressure are described above in the context of catheter-based ablation, the principles of the present invention may similarly be applied in other applications that require accurate sensing of the movement of a joint, and particularly in therapeutic and diagnostic applications that use invasive probes, both in the heart and in other organs of the body. As one example, the devices and techniques for position and pressure sensing that are implemented in system 20 may be applied, mutatis mutandis, in guiding and controlling the use of a catheter insertion sheath. If the position of the sheath is not properly controlled and excessive force is used in its insertion, the sheath may perforate the heart wall or vascular tissue. This eventuality can be avoided by sensing the position of and pressure on the distal tip of the sheath. In this regard, the term "distal tip" as used herein should be understood to include any sort of structure at the distal end of a probe that may be bent and/or displaced relative to the main body of the probe.

Figure 4:
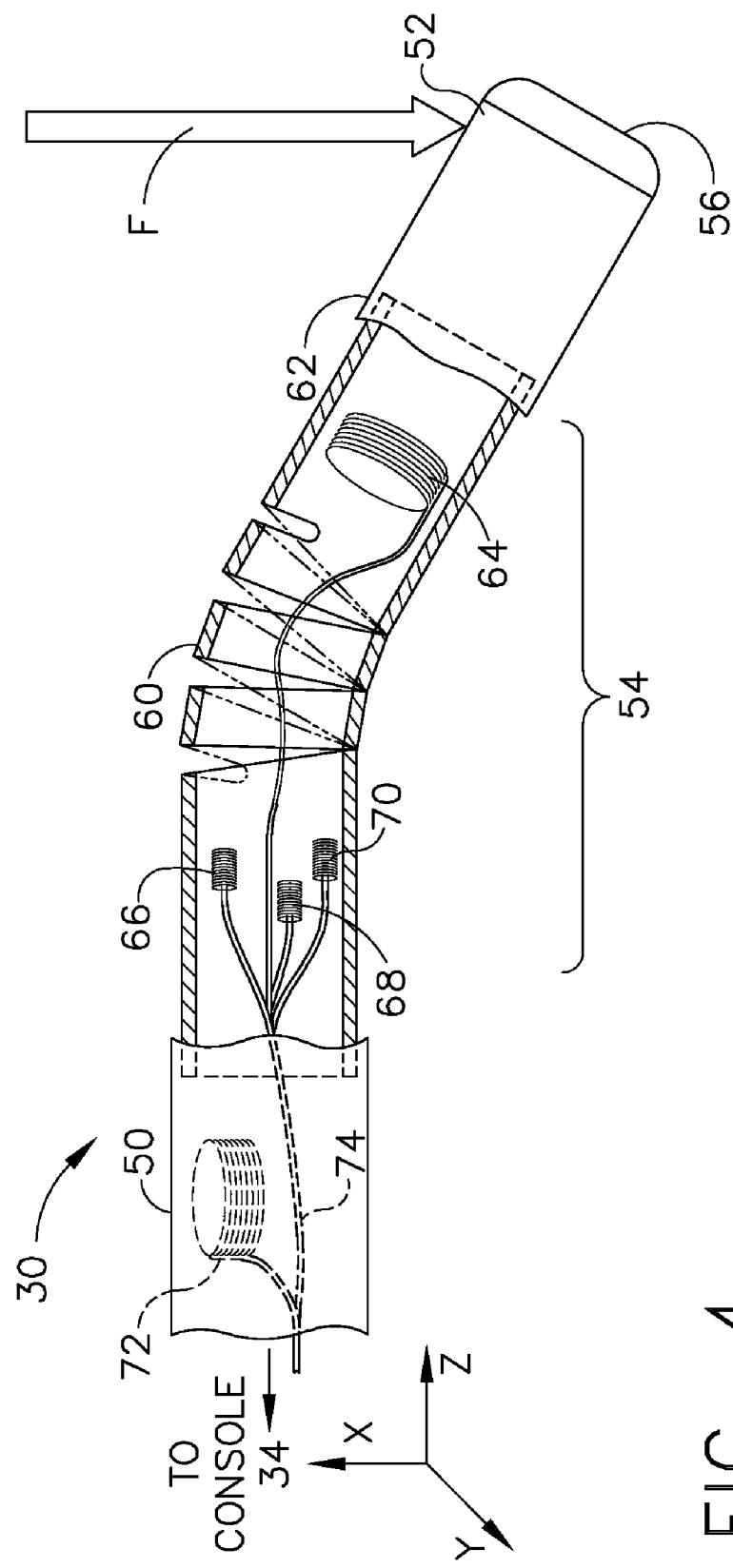
FIG. 4 is a schematic, sectional view showing details of the distal end of the catheter in FIG. 3 at its force threshold for compression, in accordance with the present invention.

As best illustrated in FIG. 4, a force F exerted on the catheter tip 52 causes joint 54 (catheter spring) to experience both axial compression and angular deflection. As outlined above, both of these dimensions of movement are taken into account for converting the tip position to force F. Beyond a certain force limit, i.e. compression threshold, however, the gaps between the windings of the spring 54 close down, as illustrated in FIG. 4, and no further compression is possible. Thus, the axial compression limit for the spring 54 is achieved which is measured at is about 30 grams for the spring design illustrated in FIGS. 3 and 4. Accordingly, any additional force F exerted on catheter tip 52 beyond the given force limit can be expressed only in deflection (up until now).

Figure 5:
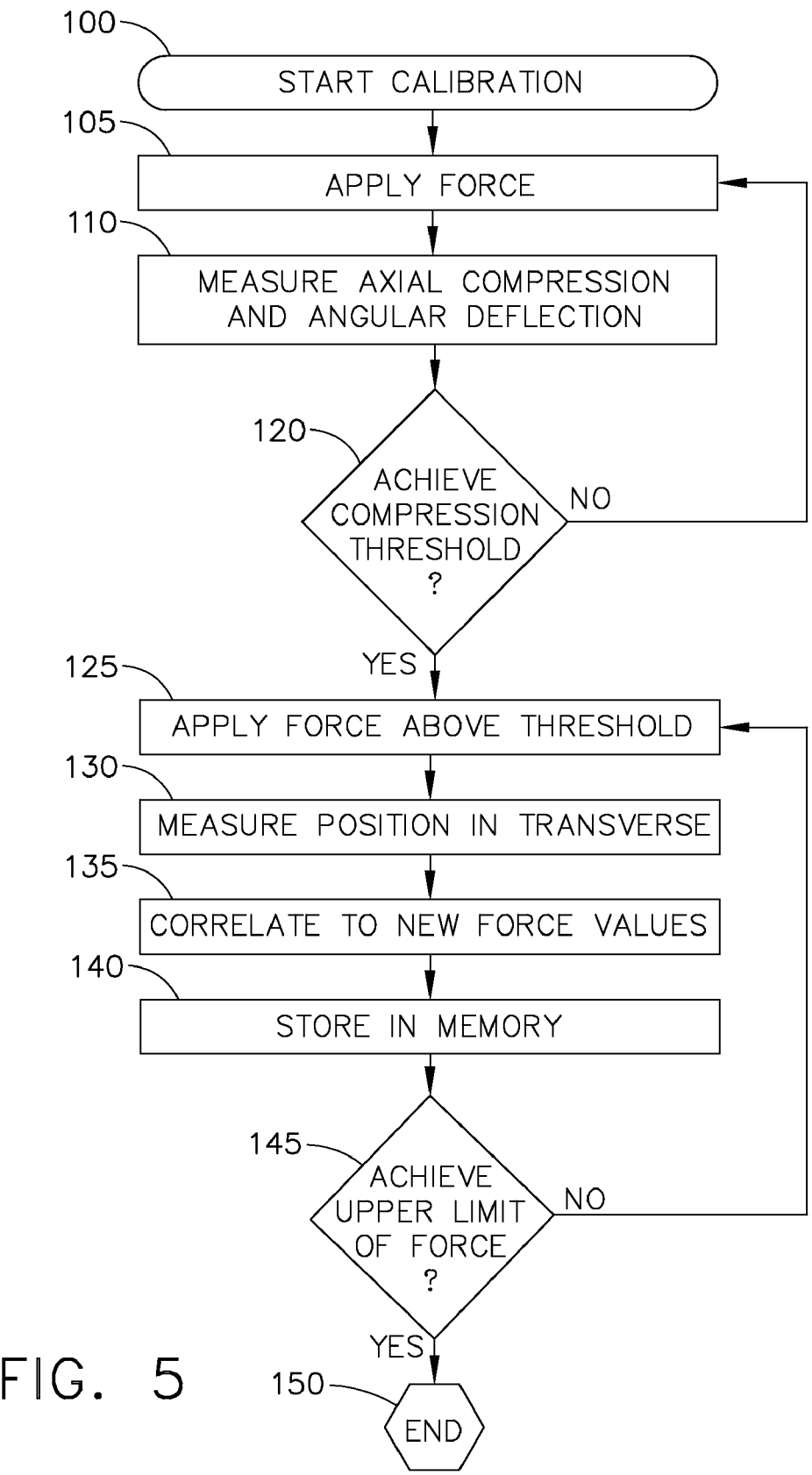
FIG. 5 is a schematic, flow chart of the force calibration method in accordance with the present invention.

However, as best illustrated in FIG. 5, the present invention is directed to a method of calibration for the catheter 30 of FIGS. 3 and 4. In addition to the force calibration procedure described earlier, a further calibration procedure (FIG. 5) is conducted in order to enhance accuracy and force measurements for very large (substantial) or extreme force F exerted on catheter tip 52. This additional calibration procedure of the present invention schematically shown in FIG. 5 is directed toward obtaining force measurements F after maximum axial compression has already been achieved (FIG. 4).

Accordingly as part of the overall calibration for the device or catheter 30 calibration is started in step 100 wherein force is applied to catheter tip 52 in step 105 wherein for various discrete force applications and measurements, a corresponding axial compression and angular deflection measurement is made and stored in calibration memory as described earlier (step 110).

Step 120 is a logic step wherein the measured axial compression is compared to the known/pre-established compression threshold or limit, for example, about 30 grams for the catheter tip design shown in FIGS. 3 and 4. If the measured axial compression is below the compression threshold, the force level F is increased in step 105, for example at discreet force intervals, and measurement and compare/logic steps of 110 and 120 respectively are repeated until the axial compression level measured has achieved, i.e. equal to or greater than, the compression threshold at step 120.

Once the axial compression threshold has been met in step 120, additional force F (force greater than the axial compression threshold limit as a new force value) is applied to tip 52 (as shown in FIG. 4) in step 125, for example at discreet force levels exceeding the compression limit or threshold for spring 54, i.e. at force levels greater than 30 grams in the embodiment of FIGS. 3 and 4.

For each discreet force application above the spring axial compression threshold (in step 125), the position coordinates of the tip 52 are measured in a plane transverse to the direction of force F in step 130. Thus, in the illustrated examples of FIGS. 3 and 4, force F is applied in X-Z axis direction and position coordinates are measured for the X-Y transverse axis or plane in step 130. These position coordinates are six-dimensions of location and orientation information, i.e. X,Y,Z axis directions and pitch, yaw and roll orientations.

In step 135, the position coordinates measured in the transverse plane, i.e. the X-Y transverse plane in this example, are correlated directly to the new force level or value F applied in step in 125 and stored in the memory of system 34 (FIG. 1) in step 140.

A further logic step 140 is conducted wherein the new force level F applied in step 125 is compared to a pre-established upper limit for force F (by test design), for example, the maximum limit above compression threshold for force F tested. One example of the test upper force limit is 60 grams of force, which is a substantial amount of force to be exerted on a catheter tip 52, especially when the axial compression threshold for the spring 54 is about 30 grams in the example provided. If the maximum force limit has not been achieved, steps 125, 130, 135, 140 and 145 are repeated until the upper limit (test limit) of force F has been reached wherein the calibration is completed at step 150.

The present invention capitalizes on the discovery that the force F on the catheter tip 52 is proportional to the magnitude of the projection of the catheter tip 52 location in the plane transverse to the direction of force (i.e., the X-Y plane in the coordinate system of FIG. 3 and FIG. 4). Thus, by measuring the catheter tip projection, i.e. measuring the position of tip 52 in the transverse plane or transverse axial direction, based on the signals output by the sensing coils 66, 68 and 70, it is sufficient to give an accurate force reading when the force F is above the spring compression threshold (in this example about 30 grams).

Therefore, in calibrating the catheter 30, the calibration model and parameters above the force threshold F are correlated directly to a measurement of the transverse axial projection of the tip (in this example the transverse plane being the X-Y axis plane) and computation of the proportionality and relationship between the applied force F and the tip projection/location (based on position coordinates). Thus, during actual operation of the device/catheter 30 in a surgical procedure (FIG. 1), accurate force measurements can be made based on the actual force being exerted on the catheter tip 52 even after the spring threshold has been achieved.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for calibrating a force measuring probe used in a medical procedure performed on a body of a patient, the method comprising the steps of:

providing a probe, comprising an insertion tube, having a longitudinal axis and a distal end, a distal tip disposed at the distal end of the insertion tube and is configured to be brought into contact with tissue of the body, a joint comprising a resilient member, which is configured to deform in response to force exerted on the distal tip when the distal tip engages tissue, the joint coupling the distal tip to the distal end of the insertion tube, and a joint sensor, contained within the probe, for sensing a position of the distal tip relative to the distal end of the insertion tube, the joint sensor comprising a first subassembly and a second subassembly, which are disposed within the probe on opposite, respective sides of the joint, wherein the first subassembly and the second subassembly comprise one or more magnetic transducers; and a processor, which is coupled to the probe for applying a current to one of the first subassembly and the second subassembly, thereby causing one of the first subassembly and the second subassembly to generate at least one magnetic field, and which is coupled to receive and process one or more signals output by the other of the first subassembly and the second subassembly responsively to the at least one magnetic field so as to detect changes in a position of the distal tip relative to the distal end of the insertion tube, wherein the changes in the position of the distal tip detected by the processor comprise an axial displacement of the distal tip and an angular deflection of the distal tip relative to the distal end of the insertion tube, and wherein the processor is configured to generate, responsively to the detected changes in the position, an output that is indicative of the force exerted on the distal tip, and a memory having an axial displacement threshold for the joint stored therein;

applying force to the distal tip;

measuring the axial displacement and the angular deflection of the distal tip;

correlating the measured axial displacement and the angular deflection of the distal tip to the applied force at the distal tip and storing the correlation in the memory until reaching the axial displacement threshold;

applying force greater than the axial displacement threshold to the distal tip to define a new force value;

measuring the position of the distal tip in a plane transverse to the direction of force exerted on the distal tip;

correlating the measured position of the distal tip in the plane transverse to the direction of force to the new force value and storing the correlation in the memory until reaching a pre-established upper limit for the new force value.

2. The method according to claim 1, further comprising providing magnetic transducers that comprise coils, wherein the first subassembly comprises a first coil having a first coil axis parallel to the longitudinal axis of the insertion tube, and wherein the second subassembly comprises two or more second coils in different, respective radial locations within a section of the probe that is spaced apart axially from the first subassembly.

3. The method according to claim 2, further comprising providing a magnetic field generator, for generating a further magnetic field in a vicinity of the body, and using at least one of the magnetic transducers in one of the first subassembly or the second subassembly as a position sensor in the probe for generating a position signal in response to the further magnetic field, wherein the processor is coupled to receive and process the position signal in order to compute position coordinates of the probe relative to a frame of reference that is separate from the probe.

4. The method according to claim 3, further comprising determining position coordinates that are six-dimensional position and orientation information.

5. The method according to claim 4, further comprising providing an axial displacement threshold that is about 30 grams force.

6. The method according to claim 5, further comprising providing a new force value that is greater than about 30 grams force.

7. The method according to claim 6, further comprising providing a probe that is a catheter.

* * * * *